United States Patent
Baermann

[11] Patent Number: 5,965,282
[45] Date of Patent: Oct. 12, 1999

[54] MAGNETIC ARRANGEMENT FOR THERAPEUTIC APPLICATION

[75] Inventor: Horst Baermann, Bergisch Gladbach, Germany

[73] Assignee: Rheinmagnet Horst Baermann GmbH, Neunkirchen, Germany

[21] Appl. No.: 08/849,436

[22] PCT Filed: Jul. 23, 1996

[86] PCT No.: PCT/DE96/01395

§ 371 Date: May 22, 1997

§ 102(e) Date: May 22, 1997

[87] PCT Pub. No.: WO97/11749

PCT Pub. Date: Apr. 3, 1997

[30] Foreign Application Priority Data

Sep. 25, 1995 [DE] Germany .......................... 295 15 302

[51] Int. Cl.[6] .................. A61M 1/00; H01F 1/00
[52] U.S. Cl. .................. 428/692; 428/900; 600/9; 600/15
[58] Field of Search .................. 428/692, 900; 600/9, 15

[56] References Cited

U.S. PATENT DOCUMENTS 5,017,185  5/1991  Baermann ................................ 600/15
5,304,111  4/1994  Mitsuno ................................... 600/9

FOREIGN PATENT DOCUMENTS

3246128A1  6/1983  Germany .
3331061A1  3/1985  Germany .
3730077A1  4/1988  Germany .
2196855    5/1988  United Kingdom .

*Primary Examiner*—Steven A. Resan
*Attorney, Agent, or Firm*—Fildes & Outland, P.C.

[57] ABSTRACT

The object of the invention is a magnetic arrangement for the treatment of surface near skin or tissue areas of the human body having several mechanically connected magnetic bodies ($M_1$, $M_2$) which build an active surface on, or in, the vicinity of which the magnetic field there present is utilized. Use has long been made in therapeutics of flexible magnets of plastic bonded hard ferrite having at least one North and one South pole on their active surface facing the body, whereby the pole configurations are arranged in different ways dependent upon the therapeutic objective. It is thus possible to generate magnetic inductions only in surface near skin or tissue areas. A magnetic arrangement of several magnetic bodies of high coercive field strength with different energy densities is proposed to attain locally restricted higher magnetic inductions.

19 Claims, 3 Drawing Sheets

MAGNETIC ARRANGEMENT FOR THERAPEUTIC APPLICATION

The invention refers to a magnetic arrangement for therapeutic application, particularly for the treatment of surface near skin or tissue areas of the human body, of one or more mechanically connected magnetic bodies which build an active surface on, or in, the vicinity of which the magnetic field there present is utilized.

Such known magnetic arrangements are, for example, shown in homogeneous permanent magnetic strips, which are magnetized with one or more poles, or in certain forms of discretely arranged permanent magnets of identical magnetic material. The permanent magnets or permanent magnetic strips may be rigid magnets, made for example of sintered hard ferrite or, also flexible magnets, for example of plastic bonded ferrite particles, whereby the particles, usually consisting of hard ferrite powder, are contained in the plastic matrix in statistically finely dispersed homogeneous form by, for example, mixing in stamping masticators. The geometrical shape, arrangement and magnetization of the magnetic bodies, as well as their magnetic material, are chosen to suit the intended application. The magnetic induction present at the active surface, or at a certain distance therefrom, is, in the case of the above mentioned magnetic arrangements, limited and in many cases it is desirable to increase the magnetic induction at, or in, the vicinity of the active surface.

Magnetic arrangements with alternating poles are known within the field of therapeutics for some time. They are rigid or flexible permanent magnets which have at least one pole on their active surface facing the body. For example, rigid magnets of this type, made of sintered hard ferrite, are largely used in Japan. Parallel to this, flexible magnets made of plastic bonded hard ferrite have been established within the field of magnetic therapeutics in Europe and the USA since 1983. These have at least one North and one South pole on their active surface facing the body, whereby the pole configurations are arranged in different ways dependent upon the therapeutic objective and are marketed by the applicant of this patent under the trade names "BIOflex" and "VITAflex". Such magnetic foils are described under EP-PS 0 134 437, U.S. Pat. No. 4,549,532 and JP-PS P1 652 939. The basic effectiveness of such magnetic arrangements on the human organism could be proven within a double blind study carried out by Dr. Jens Martin, of the Klinik Bavaria in Schaufling.

For the magnets of the above trademark "BIOflex" which are applied for therapeutic purposes, maximum induction values of up to ca. 60 mT are obtained immediately on the surface of such magnets. However, the induction of at least 1 mT, required to obtain a therapeutically relevant effect, can thereby, depending upon the material thickness of such magnets, only be obtained at an airgap (identical to the penetration depth into the body) of up to maximum, 20 mm. Depending upon the therapeutic objective, higher magnetic inductions are desired not only in the skin or tissue areas near to the surface of the body, but also in the deeper areas of more than 7 mm, particularly however, of more than 15 mm, measured from the body surface.

However, higher magnetic inductions, particularly in the case of treating larger areas, are not always tolerable. Also, in many cases, it is desired to achieve punctate magnetically induced effects in deeper positioned areas of the body in order to obtain such effects which are known from acupuncture. Since, generally, the induction values decrease with the third power to the distance from the magnet, it is imperative to use magnets with particularly high surface area induction, in order to create a sufficiently high induction in the body areas which are deeper than 20 mm.

The invention is therefore based on the objective to create higher performance magnetic arrangements of the above mentioned type with which, in particular, high local induction values can be achieved in certain areas of the effective surface, as well as a higher penetration depth in these areas of the body.

In accordance with the invention the objective is achieved, when the magnetic arrangement of at least one first magnetic body, and at least one second magnetic body mechanically connected to the first is provided, whereby the magnetic bodies show a high coercive field strength and whereby the maximum value of the product B·H ($[BH]_{max}$-value) of the first magnetic body is lower than that of the second magnetic body and the two magnetic bodies build an active surface of the magnetic arrangement, reference the intended effect of the magnetic field.

Due to the invention's objective of combining magnetic bodies of different energy density into a system, or effective unit, a stronger magnetic flux is achieved in the area of the active surface of the higher energy density second magnetic body whereas being weaker in the area of the active surface of the lower energy density first magnetic body. Depending upon the geometrical shape, arrangement and magnetization of the magnetic bodies and the choice of magnetic material, higher magnetic inductions can thus be achieved in certain areas of the active surface, or at a distance from the same.

By using the magnetic arrangement in accordance with the invention, certain tissue sections for example can purposefully be treated with high induction and higher depth effect connected thereto. Certain acupuncture points of the living organism for example can thereby be treated purposefully. By increasing the induction in only certain areas, other sections of the body will, however, be spared from the effect of the stronger magnetic field.

By using the magnetic arrangement in accordance with the invention preferable therapeutic objectives can be achieved in surface near skin or tissue areas, as well as "simultaneous" in locally restricted areas with depth effect. Because both different magnets have as high a coercive field strength as possible and are connected to one another, counter influencing or weakening of the one magnetic material by the other can, in a preferable way, largely be avoided.

The invention includes the use of mechanically connected magnetic bodies with two or more different $[BH]_{max}$-values.

The different energy densities of the magnetic bodies are preferably achieved by using different magnetic materials. The magnetic body or bodies with lower energy densities for instance, consist of barium or strontium ferrite, whereas the magnetic bodies with higher energy densities are chosen from the group of rare-earth magnets, such as $SmCo_5$ or NdFeB.

It is preferable that the $[BH]_{max}$-value of the second magnetic body be at least twice as high as that of the first magnetic body. Particularly good effects were achieved with arrangements when the $[BH]_{max}$-value of the second magnetic body is at least fifteen times higher than that of the first magnetic body.

The second magnetic body of higher energy density may be embedded into the active surface of the first magnetic body of lower energy density. Thereby a jointly aligned active surface of both magnetic bodies can be achieved.

On the other hand, the second magnetic body may also be arranged in form of a flat piece on the active surface of the first magnetic body so that the active surfaces of both magnetic bodies are arranged staggered to one another. Since in most cases the magnetic induction becomes effective at some distance from the surface, this arrangement is usually easier to produce.

In accordance with the invention several magnetic bodies of higher energy density, also differing ones, may also be arranged into, or on, the active surface of the first magnetic body. The magnetic arrangement can also include several magnetic bodies of lower energy density in, or on, which magnetic bodies of higher energy density are affixed, as explained in the foregoing example.

The active surface of the second magnetic body, or the magnetic body of higher energy density, is preferably smaller than that of the first magnetic body, or the magnetic body with lower energy density.

In order to prevent the magnetic field from straying away from the area above the active surface it is appropriate that the vector sum of all magnetic fluxes on the active surface area of the magnetic arrangement is nearly zero.

The second magnetic body may for example be form-fit embedded into a space or bore hole in the first magnetic body and secured by known fixing methods, such as glueing, welding, or covering of both sides with a coating of glue, or similar. However, due to the magnetic stray fields, a form-fit embedding is not absolutely necessary. In order to create larger ambient straying of the magnetic field it may even be favourable to provide an airgap of suitable size between the two magnetic bodies.

In the case of separated arrangement of the magnetic bodies it is appropriate to connect these on the side opposite to the active surface by a ferro-magnetic retainer layer, of low carbon soft iron or a rigid or flexible layer of non-magnetizable material, such as, for example, non-magnetic stainless steel, aluminium or plastic, or of a combination of these components.

On the other hand, the magnetic bodies which are arranged spatially separated from one another, may also be connected to one another on their active surface by a rigid or flexible layer of non-magnetizable material, for example by the above mentioned components. Therefore, rigid or elastic, or flexible layers are suitable. In addition to connecting the magnetic bodies they also serve the dimensional stability of the magnetic arrangement.

For securing the second magnetic body to the active surface of the first magnetic body it is also appropriate to provide for an intermediate layer of non-magnetizable material, such as a glue, a plastic layer or another optional non-magnetizable material, such as a fabric.

In accordance with the invention which is aligned to a largest possible straying effect of the magnetic field within the area above the active surface, such magnetic arrangements where the first magnetic body, or the magnetic bodies of lower energy density are magnetized in axial direction, i.e. vertical to their active surface are preferred. Thereby, depending upon the intended application, the magnetic body may have one or more poles on its active surface, possibly with alternating polarity and in optional arrangement. The bodies need not necessarily be magnetized in axial direction; the invention may be understood such, that any type of magnetization is feasible.

In accordance with a particularly preferred embodiment of the invention, such magnetic arrangements are suggested, whereby the first magnetic body is magnetized with one pole on its active surface, or consists of magnetic body segments with magnetized poles of identical type, arranged spaced apart from one another, and the second magnetic body, preferably several magnetic body segments of identical polarity on their active surfaces, formed in known geometrical figures and configurations, but which are of different polarity to those of the first magnetic body, embedded in the first magnetic body, or arranged between its poles, or fixed to its surface.

In general, the first magnetic body may also be magnetized on its active surface with several poles, or consist of magnetic body segments with magnetized poles of different polarity, arranged spaced apart from one another, whereby the second magnetic body, as described above, is arranged between two poles of the first magnetic body and the poles opposite to one another on both magnetic bodies having different polarity. In this case also, the magnetic arrangement consists of a pole configuration with poles of alternating polarity, whereby in the areas of the magnetic body, or magnetic bodies of higher energy density, higher magnetic induction is retained on the active surface, and whereby moreover the pole face of the magnetic bodies have the known geometrical shapes and arrangements, such as stripe-type, circular, radial, three or more cornered, segment, sickle or sun-wheel shaped or similar configurations.

Several examples of the invention's embodiments are explained in detail by drawings below. The drawings show:

FIG. 1 an embodiment of the magnetic arrangement for therapeutic purposes,

FIG. 2 a cross section along the line II—II in FIG. 1,

FIG. 3 a cross section through a second embodiment,

FIG. 4 a further embodiment of the magnetic arrangement,

FIG. 5 a variation of the embodiment according to FIG. 4,

FIG. 6 a further embodiment of the magnetic arrangement,

FIG. 7 a further embodiment of the magnetic arrangement,

FIG. 8 a plan-view of the magnetic arrangement according to FIG. 7,

FIG. 9 a variation of the embodiment according to FIG. 7,

FIG. 10 to FIG. 14 further embodiments of magnetic arrangements with differing pole configurations of the relevant bodies.

The magnetic arrangements shown in FIGS. 1 to 3 consist of a first magnetic body $M_1$ and a second magnetic body $M_2$ mechanically connected thereto, whereby the two magnetic bodies $M_1$ and $M_2$ show a high coercive field strength, the $[BH]_{max}$-value of the first magnetic body $M_1$ being lower than that of the second body $M_2$ and the two magnetic bodies $M_1$ and $M_2$ building an active surface (surface of the magnetic arrangement shown in FIGS. 1 to 3) with reference to the intended effect of the magnetic field. In the embodiment shown in FIGS. 1 and 2, the second body $M_2$ is arranged on the active surface of the first body $M_1$ in the form of a flat piece.

In the embodiment shown in FIG. 3, the second magnetic body $M_2$ is embedded into the first magnetic body $M_1$ at its active surface.

In both embodiments the active surface of the second magnetic body $M_2$ is smaller than that of the first magnetic body $M_1$. As further demonstrated in FIG. 3, the vector sum of all magnetic fluxes is zero on the active surface of both magnetic bodies $M_1$ and $M_2$.

The following two examples show different magnetic materials for the magnetic bodies $M_1$ and $M_2$ and the appropriate values for the magnetic remanence $B_r$, the coercive field strength $_iH_c$ and the maximum magnetic energy product $[BH]_{max}$.

EXAMPLE 1

$M_1$ consists of isotropic plastic bonded NdFeB.
$M_2$ consists of plastic bonded isotropic Ba-ferrite.

|  | $M_1$ | $M_2$ |
|---|---|---|
| $B_r$ [mT] | 470 | 163 |
| $_IH_c$ [kA/m] | 700 | 240 |
| $[BH]_{max}$ [kJ/m$^3$] | 35 | 4.5 |

EXAMPLE 2

$M_1$ consists of isotropic sintered NdFeB.
$M_2$ consists of anisotropic plastic bonded Sr ferrite.

|  | $M_1$ | $M_2$ |
|---|---|---|
| $B_r$ [mT] | 1,250 | 220 |
| $_IH_c$ [kA/m] | 800 | 280 |
| $[BH]_{max}$ [kJ/m$^3$] | 280 | 9.0 |

The types of embodiments shown in FIGS. 4 to 14 which are described below as examples, have proven to be particularly favourable for achieving a therapeutic effect. Thereby the magnetically higher value magnetic body $M_2$, consisting of a permanent magnetic material with elements of the group of rare-earths, such as NdFeB or SmCo$_5$, is in all cases smaller by area and volume than the magnetically lower value magnetic body $M_1$, which, for example, consists of Sr-ferrite.

In the embodiment examples circular or disc-shaped magnets are used. However, also optional other geometrical shapes, such as ovals, rectangulars, five, six or more cornered pieces, or other symmetrical or also asymmetrical tabular forms may be used.

In the magnetic arrangements shown in FIGS. 4 and 5, at least one magnetic body $M_2$ of higher energy density is arranged on the surface of a magnetic body $M_1$ of lower energy density by either direct contact (FIG. 4) or, in special cases, also by an intermediate layer $Z_1$, such as a glue, a plastic layer or other optional non-magnetizable medium, such as a fabric (FIG. 5).

The magnetic arrangement as per FIG. 6, having already been basically described in FIG. 3, shows at least one magnetic body $M_2$ of higher energy density, being integrated into a magnetic body $M_1$ of lower energy density. The magnetic body $M_2$ is inserted into a bore hole in magnetic body $M_1$ and there affixed by suitable fixing methods, such as glueing, welding, or covering of both sides with small self-adhesive discs, or similar.

In order to obtain larger ambient straying of the magnetic field, a gap is provided between the magnetic bodies $M_1$ and $M_2$, according to the magnetic arrangement shown in FIGS. 7 and 8. In the referred figures, several stripe-type magnetic bodies $M_2$ of higher energy density are arranged between several stripe-type magnetic bodies $M_1$ of lower energy density. The active surface of magnetic body $M_1$ is larger than that of magnetic body $M_2$.

The individual gap between the magnetic bodies $M_1$ and $M_2$ is preferably up to 50 mm. The magnetic bodies $M_1$ and $M_2$, consisting of different magnetic materials, are connected to one another into a circular magnetic arrangement by a rigid or elastic, i.e. flexible, connecting layer $Z_1$.

In the case of the arrangement of magnetic bodies $M_1$ and $M_2$, shown in FIG. 9 as being spatially separated from one another, a ferro-magnetic keeper layer $Z_2$, of, for example, low-carbon soft iron is provided on the side opposite to the active surface. Further, a rigid or flexible layer of non-magnetizable material, such as non-magnetic stainless steel, aluminium or a plastic, or of a combination of these components, is arranged on the active surface of magnetic bodies $M_1$ and $M_2$ which, basically, ensures the stability of the magnetic arrangement.

For the above-mentioned principle magnetic arrangements it is of no consequence which pole configuration the magnetic bodies $M_1$ and $M_2$ have on their active surface. In order to achieve the greatest possible stray effect of the magnetic field in the demonstrated embodiments the magnetic body $M_1$ is magnetized in axial direction, i.e. vertical to its effective surface.

The embodiments as per FIGS. 10 to 14 refer to other circular or rectangular magnetic arrangements whereby, as described above and shown in FIGS. 4 to 9, magnetic bodies $M_2$ of higher energy density build a mechanically connected effective unit with one or more magnetic bodies $M_1$ of lower energy density. FIGS. 12 to 14 show two embodiments which have several magnetic bodies, for example $M_2$ and $M_2'$ of higher energy density, whereby these magnetic bodies can, reference their geometric sizes and configurations and also in their energy density, be different. By this method the magnetic flux density on the active surface, and the magnetic stray field can be intensified and varied, so that these capacities may be even better adjusted to the individual application case and thereby achieve certain effects.

I claim:

1. Magnetic arrangement for therapeutic application, particularly for the treatment of surface near skin or tissue areas of the human body, with at least one first magnetic body ($M_1$) and at least one second magnetic body ($M_2$) being mechanically connected to the first, whereby the magnetic bodies ($M_1$, $M_2$) show a high coercive field strength, wherein a maximum magnetic energy product value, B·H, of the first body ($M_1$) is lower than that of the second body ($M_2$) and the bodies ($M_1$, $M_2$) form an active surface of the magnetic arrangement, said active surface being the surface area of the magnetic arrangement that is brought into contact with the human body.

2. Magnetic arrangement as per claim 1, wherein both magnetic bodies ($M_1$, $M_2$) consist of different magnetic material.

3. Magnetic arrangement as per claim 2, wherein the first magnetic body ($M_1$) consists of barium or strontium ferrites and the second magnetic body ($M_2$) consists of a permanent magnetic material and at least one rare earth element.

4. Magnetic arrangement as per claim 1, wherein the maximum magnetic energy product value of the second magnetic body ($M_2$) is at least double that of the first magnetic body ($M_1$).

5. Magnetic arrangement as per claim 4, wherein the maximum magnetic energy product value of the second body ($M_2$) is at least fifteen times that of the first magnetic body ($M_1$).

6. Magnetic arrangement as per claim 1, wherein the second magnetic body ($M_2$) is embedded into the active surface of the first magnetic body ($M_1$).

7. Magnetic arrangement as per claim 6, wherein the active surface of the second magnetic body ($M_2$) is smaller than the first magnetic body ($M_1$).

8. Magnetic arrangement as per claim 6, wherein the second magnetic body ($M_2$) is embedded into the first magnetic body ($M_1$).

9. Magnetic arrangement as per claim 6, wherein an airgap is arranged between the first and the second magnetic body ($M_1$ respectively $M_2$).

10. Magnetic arrangement as per claim 9, wherein both magnetic bodies ($M_1$, $M_2$) are connected to one another on the side opposite to the active surfaces, by a ferro-magnetic retainer layer ($Z_2$) or a rigid, or flexible, layer ($Z_1$) of non-magnetizable material.

11. Magnetic arrangement as per claim 9, wherein both magnetic bodies ($M_1$, $M_2$) are connected to one another on the active surface by a layer ($Z_3$) of non-magnetizable material.

12. Magnetic arrangement as per claim 6, wherein the first magnetic body ($M_1$) is magnetized vertically relative to its active surface.

13. Magnetic arrangement as per claim 1, wherein the second magnetic body ($M_2$) is arranged on the active surface of the first magnetic body ($M_1$) in the form of a flat piece.

14. Magnetic arrangement as per claim 13, wherein the second magnetic body ($M_2$) is connected to the first magnetic body ($M_1$) with an intermediate layer ($Z_1$) of non-magnetizable material.

15. Magnetic arrangement as per claim 13, wherein the active surface of the second magnetic body ($M_2$) is smaller than that of the first magnetic body ($M_1$).

16. Magnetic arrangement as per claim 1, wherein the vector sum of all magnetic fluxes on the active surface of the total magnetic arrangement approaches zero.

17. Magnetic arrangement as per claim 1, wherein the first magnetic body ($M_1$) is a rigid permanent magnet of sintered hard ferrite.

18. Magnetic arrangement as per claim 1, wherein the first magnetic body ($M_1$) is a flexible permanent magnet of plastic bonded hard ferrite.

19. Magnetic arrangement as per claim 1, for therapeutic application in particular, wherein the first magnetic body ($M_1$) is magnetized with one pole on its active surface, or consists of body segments with magnetized poles of identical polarity, arranged apart from one another, and the second magnetic body ($M_2$) has several magnetic body segments of identical polarity, but differing to those on the active surface of the first magnetic body ($M_1$), which are arranged in known geometrical figures and arrangements embedded in the first magnetic body ($M_1$), or arranged between its poles, or fixed to the surface.

* * * * *

(12) REEXAMINATION CERTIFICATE (4572nd)
United States Patent
Baermann

(10) Number: US 5,965,282 C1
(45) Certificate Issued: May 7, 2002

(54) MAGNETIC ARRANGEMENT FOR THERAPEUTIC APPLICATION

(75) Inventor: Horst Baermann, Bergisch Gladbach (DE)

(73) Assignee: Rheinmagnet Horst Baermann GmbH, Neunkirchen (DE)

Reexamination Request:
No. 90/005,767, Jul. 12, 2000

Reexamination Certificate for:
Patent No.: 5,965,282
Issued: Oct. 12, 1999
Appl. No.: 08/849,436
Filed: May 22, 1997

(22) PCT Filed: Jul. 23, 1996
(86) PCT No.: PCT/DE96/01395
   § 371 Date: May 22, 1997
   § 102(e) Date: May 22, 1997
(87) PCT Pub. No.: WO97/11749
   PCT Pub. Date: Apr. 3, 1997

(30) Foreign Application Priority Data

Sep. 25, 1995 (DE) .................... 295 15 302 U

(51) Int. Cl.$^7$ .............. A61N 2/08; H01F 1/00
(52) U.S. Cl. .......... 428/692; 428/900; 600/9; 600/15
(58) Field of Search .................. 428/692, 900; 600/9, 15

(56) References Cited

U.S. PATENT DOCUMENTS 4,549,532 A * 10/1985 Baermann .............. 128/1.3
5,017,185 A    5/1991 Baermann .............. 600/15
5,304,111 A    4/1994 Mitsuno ................ 600/9
5,450,858 A *  9/1995 Zablotsky et al. ...... 128/876
5,782,743 A *  7/1998 Russell ................ 600/9

FOREIGN PATENT DOCUMENTS

| DE | 1564315    | * | 3/1966  |
| DE | 3246128 A1 |   | 6/1983  |
| DE | 3331061 A1 |   | 3/1985  |
| DE | 3419055    | * | 11/1985 |
| DE | 3730077 A1 |   | 4/1988  |
| GB | 2196855    |   | 5/1988  |

OTHER PUBLICATIONS

Philpott, Biomagnetic Handbook, "Today's Introduction to The Energy Medicine of Tomorrow", Enviro–Tech Products, pp. 40–41 (1990).

* cited by examiner

Primary Examiner—Stevan A. Resan

(57) ABSTRACT

The object of the invention is a magnetic arrangement for the treatment of surface near skin or tissue areas of the human body having several mechanically connected magnetic bodies ($M_1$, $M_2$) which build an active surface on, or in, the vicinity of which the magnetic field there present is utilized. Use has long been made in therapeutics of flexible magnets of plastic bonded hard ferrite having at least one North and one South pole on their active surface facing the body, whereby the pole configurations are arranged in different ways dependent upon the therapeutic objective. It is thus possible to generate magnetic inductions only in surface near skin or tissue areas. A magnetic arrangement of several magnetic bodies of high coercive field strength with different energy densities is proposed to attain locally restricted higher magnetic inductions.

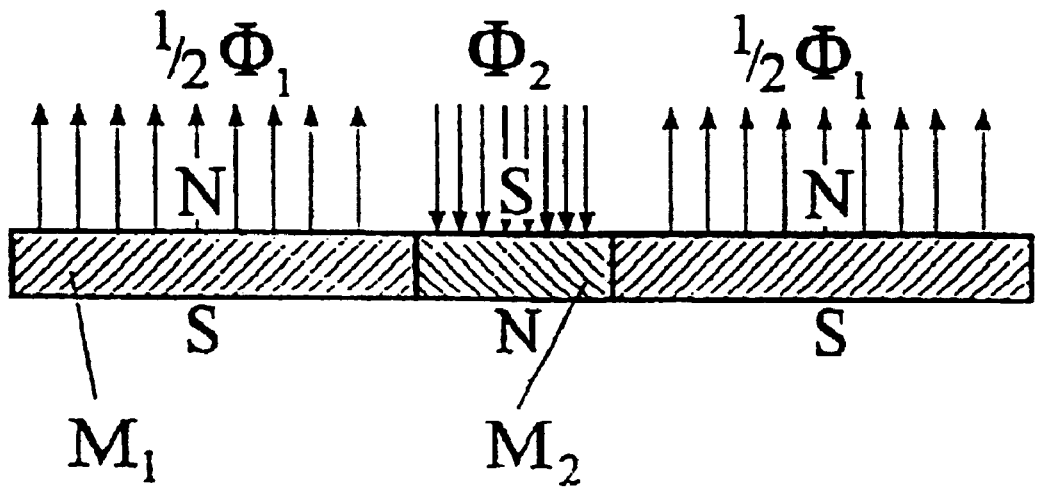

REEXAMINATION CERTIFICATE ISSUED UNDER 35 U.S.C. 307

Figure 1:
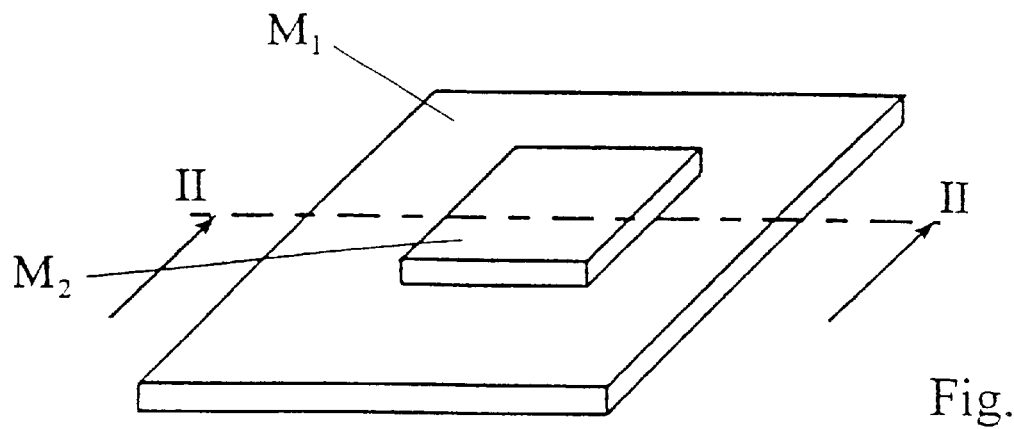
Figure 2:
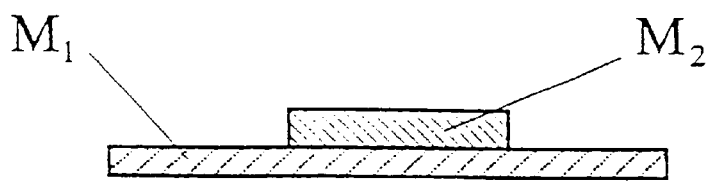
Figure 3:
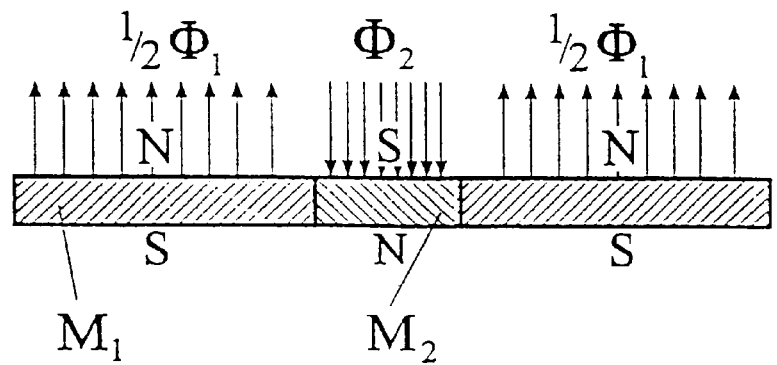
Figure 4:
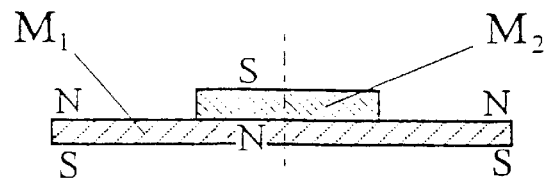
Figure 5:
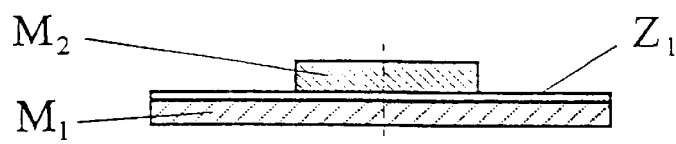
Figure 6:
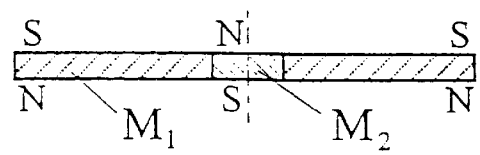
Figure 7:
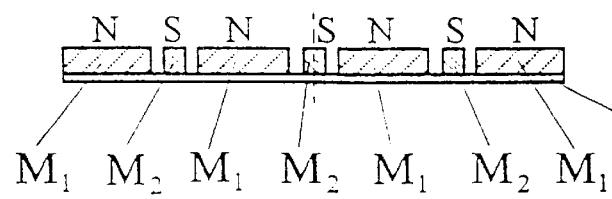
Figure 8:
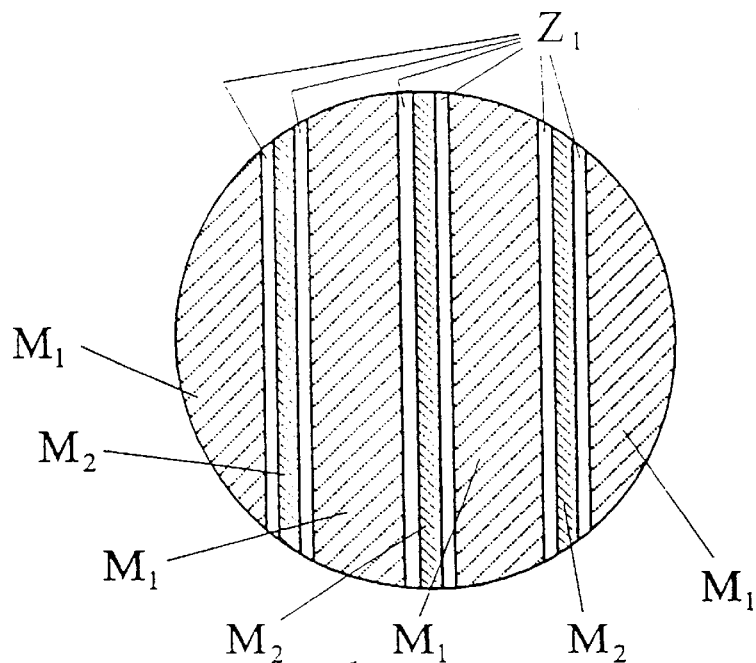
Figure 9:
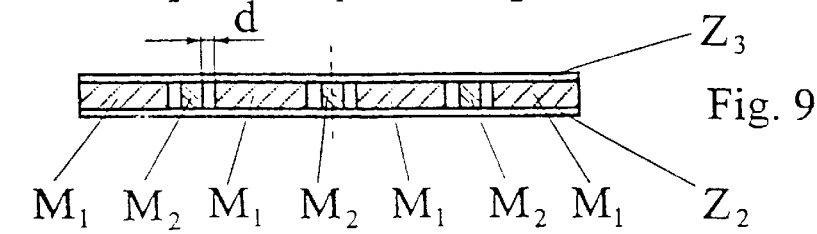
Figure 10:
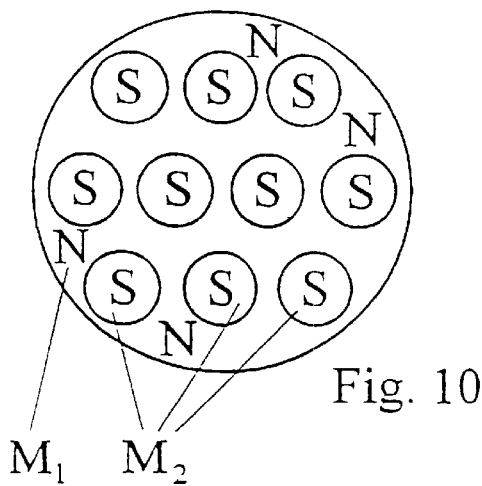
Figure 11:
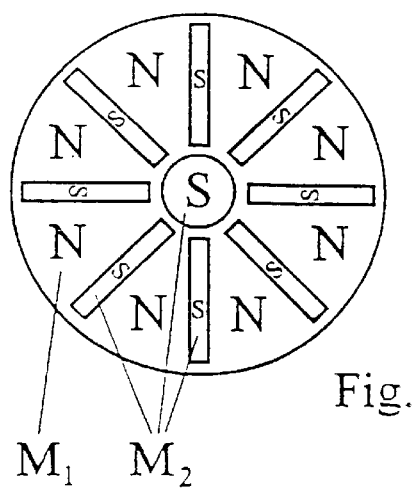
Figure 12:
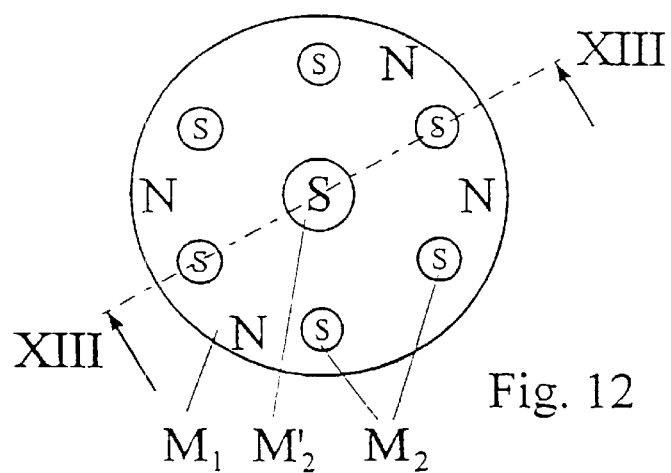
Figure 13:
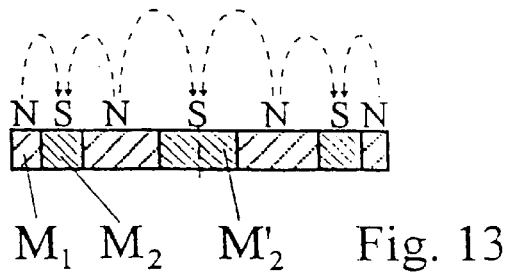
Figure 14:
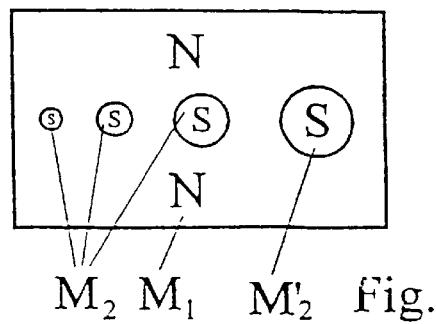

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 8 and 13–15 are cancelled.

Claims 1, 3 and 19 are determined to be patentable as amended.

Claims 4–7, 9–12 and 16–18, dependent on an amended claim, are determined to be patentable.

New claim 20 is added and determined to be patentable.

1. [Magnetic] *A therapeutic device comprising a magnetic* arrangement for therapeutic application, particularly for the treatment of surface near skin or tissue areas of the human body, with at least one first magnetic body ($M_1$) and at least one second magnetic body ($M_2$) being mechanically connected to the first[,] *magnetic body ($M_1$), wherein the* magnetic bodies ($M_1$, $M_2$) consist of different magnetic *material, and* whereby the magnetic bodies ($M_1$, $M_2$) show a high coercive field strength, wherein a maximum magnetic energy product value, B·H, of the first body ($M_1$) is lower than that of the second body ($M_2$) and the bodies ($M_1$, $M_2$) *have respective active surface regions which* form [an] *a jointly aligned* active surface of the magnetic arrangement, said active surface being the surface area of the magnetic arrangement that is brought into contact with the human body.

3. Magnetic arrangement as per claim [2] *1*, wherein the first magnetic body ($M_1$) consists of barium or strontium ferrites and the second magnetic body ($M_2$) consists of a permanent magnetic material and at least one rare earth element.

19. Magnetic arrangement as per claim 1, [for therapeutic application in particular,] wherein the first magnetic body ($M_1$) is magnetized with one pole on its active surface, or consists of body segments with magnetized poles of identical polarity, arranged apart from one another, and the second magnetic body ($M_2$) has several magnetic body segments of identical polarity, but differing to those on the active surface of the first magnetic body ($M_1$), which are arranged in known geometrical figures and arrangements embedded in the first magnetic body ($M_1$), or arranged between its poles[, or fixed to the surface].

*20. Magnetic arrangement as per claim 1, having at least one north pole on the active surface of the magnetic arrangement and at least one south pole on the active surface of the magnetic arrangement.*

* * * * *